United States Patent [19]

Iwatschenko

[11] Patent Number: 4,753,639

[45] Date of Patent: Jun. 28, 1988

[54] CONTAINER FOR THE APPORTIONING IN ENTERIC FEEDING

[75] Inventor: Peter Iwatschenko, Neunkirchen, Fed. Rep. of Germany

[73] Assignee: Pfrimmer-Viggo GmbH + Co. KG, Erlangen, Fed. Rep. of Germany

[21] Appl. No.: 38,380

[22] Filed: Apr. 15, 1987

[30] Foreign Application Priority Data

Apr. 16, 1986 [DE] Fed. Rep. of Germany ....... 3612718

[51] Int. Cl.[4] ....................... A61M 31/00; A61B 19/00

[52] U.S. Cl. .................................... 604/246; 604/262; 604/407; 222/23

[58] Field of Search ............... 604/246, 262, 244, 257, 604/260, 407, 403, 404, 408–410; 222/23, 49

[56] References Cited

U.S. PATENT DOCUMENTS 3,204,633 9/1965 Hofstra ................................ 604/246

4,435,179 3/1984 Walker ................................ 604/244

4,588,402 5/1986 Igari et al. ........................... 604/408

*Primary Examiner*—C. Fred Rosenbaum

*Assistant Examiner*—H. Macey

*Attorney, Agent, or Firm*—Jordan and Hamburg

[57] ABSTRACT

A container of flexible material for receiving and apportionately discharging liquid through an outflow opening for the purpose of enteral feeding, has arranged therein a tube of hard material, the tube being connected at one of its ends to the outflow connection of the container and being provided at specified distances with notches serving as intended breaking points.

7 Claims, 1 Drawing Sheet

CONTAINER FOR THE APPORTIONING IN ENTERIC FEEDING

This invention relates to a container of flexible material for receiving and apportionedly dispensing liquid food through an outflow opening for the purpose of enteral feeding.

In enteral feeding the patient is administered predetermined quantities of substance over a period of time. These preparations are placed into a container of specified volume and apportionedly removed from the container, whereby provisional measures have to be taken because the patent frequently is not confined to bed, but can move around and thereby also has to keep moving around with the container with the liquid food. Various pouch-like containers of flexible artificial materials are being used which usually can hold filling quantities of up to 1000 ml and allow dispensing of the contents in allotted portions of respectively very specific amounts, so that at specified time periods, the patient can easily avail himself of the individually indicated food quantities as prescribed by the doctor without requiring anybody else's help. The container which receives the substance serves thereby not only as a supply container, but it is also equipped so that it permits an apportioned dispensation. Thus, it is already known to provide such a flexible container having a separation wall extending partially into the inside of the container, thus separating a chamber from the total container volume, however, which chamber permanently communicates with the general container volume. This separation wall extends, for example, transversely into the container space and is filled with the content at the normal upright orientation of the container. If the container is turned by 90°, so that the separation wall is arranged in an upright position on the inside of the container space, it is possible by a simple tipping of the container to accumulate a specific amount of substance in the chamber which the separation wall separates from the remaining volume of the container. Because of a graduation which is applied onto the container wall, it is possible, without problems, to determine the quantity of such a portion. Subsequently, when the outflow opening or the tube connected thereto is opened, the allotted quantity of substance previously accumulated in the chamber can flow out of the container. Thereafter, the tube is shut off again, and the container can again be arranged without problems in its normal upright position.

A different, however, essentially similarly designed container is provided with a clamp which permits separation of a volume from the entire container contents adjacent to the outflow opening, which volume is again indicated by a graduation. Because of the flexibility of such containers, it is possible without any problems to clamp-off such a partial volume from the remaining inner space of the container. When the outflow opening is opened or the tube passage is freed, only the content of the volume of the clamped-off portion of the container exits. Depending on the quantity of the portion, the clamp is placed at a corresponding location which is marked by a graduation. Also in this case, in order to keep the length of the clamp as short as possible, the inside space of the container can be subdivided by a separation wall whereby, however, as before, the chamber separated from the container volume can communicate with the remaining inner space of the container. There is the problem, however, that the clamp gets lost and, thus, the container is of limited use.

The useability of such containers is especially important because the patient is already impaired due to the enteral feeding. The patient should be equipped with instruments which are as practical as possible to handle and which reduce his handicap as much as possible.

A special object of this invention is directed to providing a container of the initially mentioned kind for use in enteral feeding. According to the invention, the object is solved in that on the inside of the container there is arranged a tube made of hard plastic and connected at one of its ends to the outflow opening and provided at specified distances with notches which serve as intended breaking points.

Such a container can always be held in one and the same orientation, i.e., in the upright position, or also be taken along by the patient, and it is no longer required that the patient carry out a manipulation which requires a certain agility in order to subdivide the predetermined quantity of the substance within the container before removing the substance from the container and introducing it into the digestive tract. Rather, the invention provides the possibility to attain a reduction of the length of the tube, that is, for it to be shortened to such an extent as required for the individual portion to be administered. The utilization of a hard or brittle, however, in any event, breakable material for the tube arranged inside the container makes it possible, in particular in connection with a flexible container configuration, to break off one or more parts of the inner free tube end marked by breaking points. The broken off piece remains inside the container without thereby causing any interference. The height of the inflow opening of the tube is thereby reduced and the substance located above that level inside the container can now enter without problems into the tube and be removed from the container.

It is within the scope of the invention that the distance between the notches of the tube correspond to the difference of the surface level of the filling volume for a minimum portion. If greater portions are to be administered simultaneously, the user breaks off a longer piece of the tube or several individual consecutive pieces of the tube.

Furthermore, it is also within the scope of the invention that in a container of transparent flexible material, as is generally the case, the tube itself is provided with an imprint showing the portion quantity. Of course, the imprint can also be provided on the wall of the container. However, the marking for the intended breaking points on the tube arranged inside the container serve for the reliable handling of the apparatus and facilitates its use even for the less dexterous patient.

Further characteristics, details and advantages of the invention result from the following description of a preferred embodiment of the invention as well as from the accompanying drawings.

DESCRIPTION OF THE PREFERRED EMBODIMENTS

Figure 1:
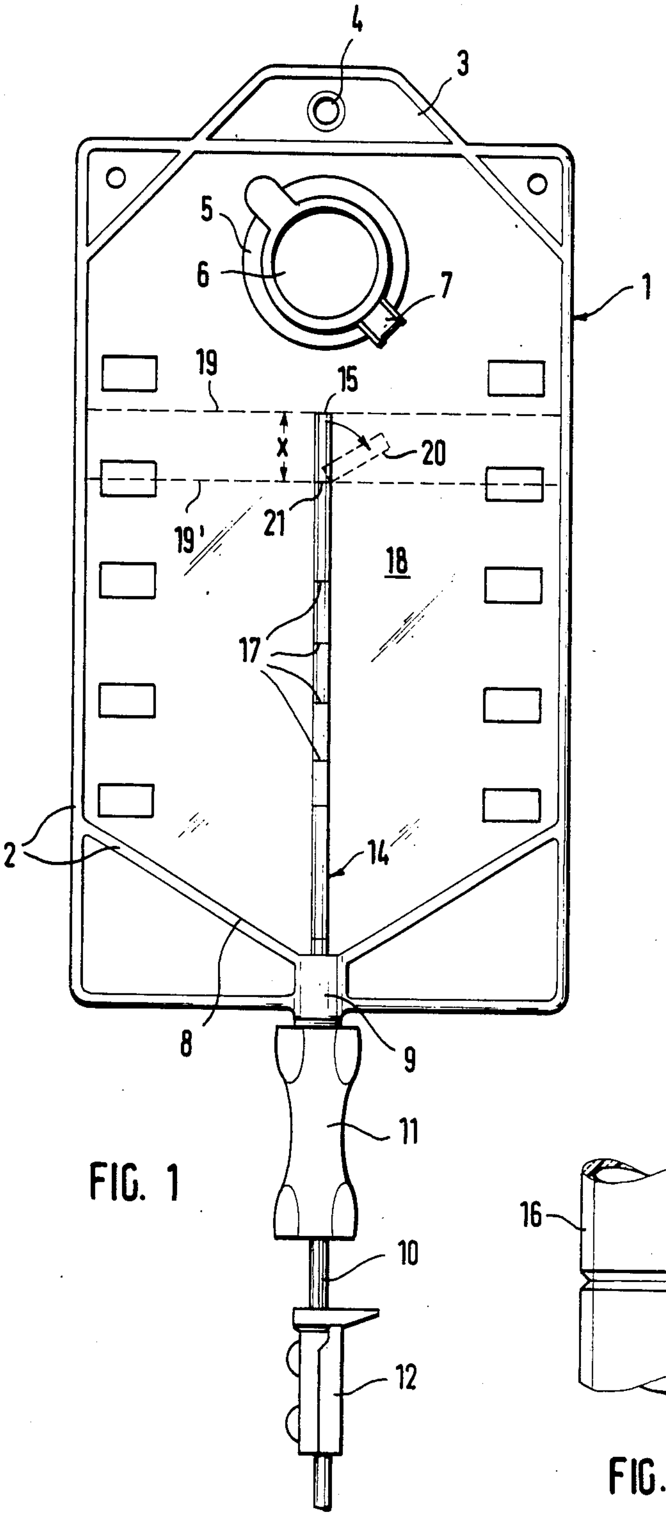
FIG. 1 is a top view of a container according to one embodiment of the invention.
Figure 2:
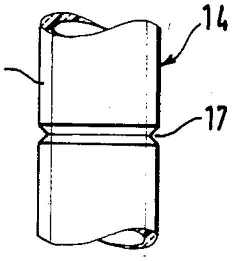
FIG. 2 is a detail of the container shown in an enlarged scale.

A container 1 consists of a flexible, physiologically compatible material, such as, for example, PVC. The volume of the container is determined by welding seams 2. At the top end is formed a flap 3 which is provided with a lug 4 for suspending the container 1. At the top the container 1 is provided with a filling opening 5 which can be closed by a cover 6 which is formed with the container 1 by a connecting part 7. The bottom 8 of the container 1 extends conically towards an outflow opening 9 to which a tube 10 is connected and which can be provided, for example, with a filter 11 and a tube clamp 12 by means of which the passage of the liquid through the tube 10 can be reliably blocked. To this outflow connection 9 there is connected a tube 14 which is made of a harder plastic than the flexible material of the container 1, for example, ABS or the like. The upper end 15 of the tube 14 is open towards the inner space of the container. At specified distances, annular notches 17 are formed in the wall 16 of the tube, whereby each marking serves as an intended breaking point. The distance between the individual notches 17 determines in each case a portion of the substance contained in the container 1. This quantity can be marked by an imprint on the outer wall 18 of the container 1 or also on the wall 16 of the tube.

When the container 1 is being filled the tube 14, for example, has a length as can be seen in FIG. 1 and the mouth 15 of the tube 14 is at the height of the level 19 at maximum filling. The container content can amount, for example, to 1000 ml. Again for example, if a quantity of 100 ml is to be removed, thus corresponding to a difference x between the levels, the user breaks off only the uppermost part 20 of the tube 14 in the area of the notch marked by 21. When the tube clamp 12 is opened, the liquid can enter into the tube 14, that is, until the filling level 19 of the liquid has sunk to the level 19'. At specified time periods the user can repeat this procedure, thereby shortening the tube 14 each time to such an extent as is required for the portion of the content of the container 1 to be administered.

I claim:

1. An enteral feeding device comprising a container of flexible material for receiving and dispensing liquid nutrients, an outlet opening in said container for discharging said liquid nutrients form said container, a tube disposed in said container and connected to said outlet opening, said tube being made of a hard material, and spaced notch means on said tube which provide intended breaking points on said tube to thereby provide for apportioned dispensation of said liquid nutrients from said container.

2. An enteral feeding device according to claim 1 wherein said notch means are spaced at a distance from one another corresponding to a minimum apportioned volume of liquid nutrients to be dispensed.

3. An enteral feeding device according to claim 1 further comprising indicia means on said tube juxtaposed to said notches indicating the apportioned volume of liquid nutrients to be dispensed.

4. An enteral feeding device according to claim 1 further comprising indicia means on said container generally aligned with said notch means to indicate the apportioned volume of liquid nutrients to be dispensed.

5. An enteral feeding device according to claim 1 wherein said container has a top and a bottom and is vertically disposed during dispensing of liquid nutrients, said outlet opening being disposed at the bottom of said container, said tube having a longitudinal axis which is generally vertically disposed during dispensing of liquid nutrients.

6. An enteral feeding device according to claim 1 wherein said notch means comprise circumscribing grooves in said tube.

7. An enteral feeding device according to claim 6 wherein said groves have a generally V-shaped cross-sectional configuration.

* * * * *